US009532890B2

(12) United States Patent
Boyle et al.

(10) Patent No.: US 9,532,890 B2
(45) Date of Patent: Jan. 3, 2017

(54) IMPLANTABLE EXPANDABLE MEDICAL DEVICES HAVING REGIONS OF DIFFERENTIAL MECHANICAL PROPERTIES AND METHODS OF MAKING SAME

(71) Applicant: Advanced Bio Prosthetic Surfaces, Ltd., a wholly owned subsidiary of Palmaz Scientific, Inc., Dallas, TX (US)

(72) Inventors: Christopher T. Boyle, Flushing, NY (US); Christopher E. Banas, Breckenridge, CO (US); Denes Marton, San Antonio, TX (US)

(73) Assignee: Vactronix Scientific, Inc., Fremont, CA (US)

( * ) Notice: Subject to any disclaimer, the term of this patent is extended or adjusted under 35 U.S.C. 154(b) by 0 days.

(21) Appl. No.: 14/019,123

(22) Filed: Sep. 5, 2013

(65) Prior Publication Data
US 2014/0067043 A1 Mar. 6, 2014

Related U.S. Application Data

(60) Continuation of application No. 11/157,147, filed on Jun. 20, 2005, now Pat. No. 8,529,616, and a division
(Continued)

(51) Int. Cl.
*A61F 2/89* (2013.01)
*A61F 2/91* (2013.01)
(Continued)

(52) U.S. Cl.
CPC . *A61F 2/89* (2013.01); *A61F 2/91* (2013.01); *A61F 2/915* (2013.01); *A61L 31/022* (2013.01);
(Continued)

(58) Field of Classification Search
CPC .. A61L 31/022; A61L 2/89; A61L 2250/0042; A61L 31/14
See application file for complete search history.

(56) References Cited

U.S. PATENT DOCUMENTS

| 4,665,906 A | 5/1987 | Jervis ............................. 128/92 |
| 4,739,762 A | 4/1988 | Palmaz ......................... 128/343 |

(Continued)

FOREIGN PATENT DOCUMENTS

| EP | 0 145 166 | 6/1985 | ............... A61F 5/00 |
| JP | 10-500595 | 1/1998 | ............ A61M 29/00 |

(Continued)

OTHER PUBLICATIONS

Arndt, et al., "Modeling and numerical simulation of martensitic transformation in shape memory alloys" *Continuum Mechanics and Thermodynamics* 15(5): 463-485 (2003).
(Continued)

*Primary Examiner* — Thomas McEvoy
(74) *Attorney, Agent, or Firm* — David G. Rosenbaum; Benjamin D. Rotman; Rosenbaum IP, P.C.

(57) ABSTRACT

An implantable expandable medical device in which selected regions of the device are in a martensite phase and selected regions are in an austenite phase. The martensitic regions exhibit pseudoplastic behavior in vivo and may be deformed without recovery under in vivo body conditions. In contrast the austenitic regions exhibit superelastic behavior in vivo and will recover their pre-programmed configuration upon deformation or release of an applied strain.

18 Claims, 3 Drawing Sheets

Related U.S. Application Data of application No. 10/303,376, filed on Nov. 25, 2002, now Pat. No. 6,923,829.

(51) Int. Cl.
*A61F 2/915* (2013.01)
*A61L 31/02* (2006.01)
*A61L 31/14* (2006.01)

(52) U.S. Cl.
CPC ...... *A61L 31/14* (2013.01); *A61F 2002/91541* (2013.01); *A61F 2002/91558* (2013.01); *A61F 2210/0023* (2013.01); *A61F 2250/0042* (2013.01)

(56) References Cited

U.S. PATENT DOCUMENTS

| | | | |
|---|---|---|---|
| 5,190,546 A | 3/1993 | Jervis | 606/78 |
| 5,508,116 A | 4/1996 | Barrett | 428/567 |
| 5,597,378 A | 1/1997 | Jervis | 606/78 |
| 6,027,526 A | 2/2000 | Limon et al. | 623/1 |
| 6,059,810 A | 5/2000 | Brown | 606/108 |
| 6,086,599 A | 7/2000 | Lee et al. | 606/108 |
| 6,165,292 A | 12/2000 | Abrams et al. | 148/563 |
| 6,190,404 B1 | 2/2001 | Palmaz et al. | 623/1.15 |
| 6,203,569 B1 | 3/2001 | Wijay | 623/1.15 |
| 6,258,182 B1 | 7/2001 | Schetky et al. | 148/402 |
| 6,264,687 B1 | 7/2001 | Tomonto | 623/1.16 |
| 6,296,622 B1 | 10/2001 | Kurz et al. | 604/93.01 |
| 6,306,141 B1 | 10/2001 | Jervis | 606/78 |
| 6,330,884 B1 | 12/2001 | Kim | 128/898 |
| 6,375,458 B1 | 4/2002 | Moorleghem | 433/2 |
| 6,379,383 B1 | 4/2002 | Palmaz et al. | 623/1.49 |
| 6,416,543 B1 | 7/2002 | Hilaire et al. | 623/1.15 |
| 6,425,855 B2 | 7/2002 | Tomonto | 600/36 |
| 6,451,049 B2 | 9/2002 | Vallana et al. | 623/1.15 |
| 6,451,052 B1 | 9/2002 | Burmeister et al. | 623/1.16 |
| 6,485,507 B1 | 11/2002 | Walak et al. | 623/1.15 |
| 6,527,938 B2 | 3/2003 | Bales et al. | 205/229 |
| 6,530,951 B1 | 3/2003 | Bates et al. | 623/1.45 |
| 6,533,905 B2 | 3/2003 | Johnson et al. | 204/192.15 |
| 6,537,310 B1 | 3/2003 | Palmaz et al. | 623/1.13 |
| 6,579,310 B1 | 6/2003 | Cox et al. | 623/1.15 |
| 6,689,159 B2 | 2/2004 | Lau et al. | 623/1.16 |
| 6,709,454 B1 | 3/2004 | Cox et al. | 623/1.16 |
| 6,936,066 B2 | 8/2005 | Palmaz et al. | 623/1.13 |
| 2001/0001834 A1 | 5/2001 | Palmaz et al. | 623/1.15 |
| 2001/0009169 A1 | 7/2001 | Kajiwara et al. | 148/563 |
| 2001/0021870 A1 | 9/2001 | Edwin et al. | 623/1.13 |
| 2002/0017503 A1 | 2/2002 | Banas et al. | 219/69.11 |
| 2002/0052646 A1* | 5/2002 | Fischell et al. | 623/1.15 |
| 2002/0072793 A1 | 6/2002 | Rolando et al. | 623/1.16 |
| 2002/0183831 A1 | 12/2002 | Rolando et al. | 623/1.15 |
| 2003/0004567 A1 | 1/2003 | Boyle et al. | 623/1.16 |
| 2003/0059640 A1 | 3/2003 | Marton | 428/544 |
| 2003/0083646 A1 | 5/2003 | Sirhan et al. | 604/891.1 |
| 2003/0093141 A1 | 5/2003 | Dimatteo | 623/1.13 |
| 2003/0105513 A1 | 6/2003 | Moriuchi et al. | 623/1.15 |
| 2004/0014253 A1 | 1/2004 | Gupta et al. | 428/48 |
| 2004/0186554 A1 | 9/2004 | Banas et al. | 623/1.15 |
| 2006/0079953 A1 | 4/2006 | Gregorich et al. | 623/1.15 |

FOREIGN PATENT DOCUMENTS

| | | | |
|---|---|---|---|
| JP | 2000-167065 | 6/2000 | A61M 29/02 |
| JP | 2002-506365 | 2/2002 | A61F 2/06 |
| JP | 2003-199833 | 7/2003 | A61M 29/02 |
| WO | WO 99/04053 | 1/1999 | C22F 1/10 |
| WO | WO 00/69359 | 11/2000 | A61C 3/00 |
| WO | WO 01/08600 | 2/2001 | A61F 2/06 |
| WO | WO 01/35865 | 5/2001 | A61F 2/06 |
| WO | WO 01/74274 | 10/2001 | A61F 2/06 |
| WO | WO 01/87371 | 11/2001 | A61L 27/42 |
| WO | 02/064019 | 8/2002 | |
| WO | WO 02/087690 | 11/2002 | A61N 1/05 |

OTHER PUBLICATIONS

Busch, et al., "Shape memory properties in Ni—Ti sputter-deposited film" *J Appl. Phys* 68(12): 6224-6226 (1990).

"MEMS Thin Film Deposition Processes", http://www.memsnet.org/mems/beginner/deposition/.html. pp: 1-5 (2002).

Miyazaki, et al., "Martensitic transformation and shape memory behavior in sputter-deposited TiNi-base thin films" *Materials Science and Engineering* (1999).

NDC (Nitinol Devices and Components), "Nitinol technology" www.nitinol.com/3techh.html. pp: 1-3 (2002).

Prokoshkin, et al., "Structural mechanisms of high-temperature shape changes in titanium-nickel alloys after low-temperature thermomechanical treatment" *Canadian Metallurgical Quarterly* 39(2): 225-234 (2000).

"Shape Memory Alloy Transformation Temperatures", http://www.aerofit.com/sma/hysteresis.html. pp: 1-2.

Takeda, et al., "Composition control of NiTi shape memory alloy films formed by sputter deposition with a composite target" *Japanese Journal of Applied Physics* 39-1(10): 5992-5994 (2000).

\* cited by examiner

IMPLANTABLE EXPANDABLE MEDICAL DEVICES HAVING REGIONS OF DIFFERENTIAL MECHANICAL PROPERTIES AND METHODS OF MAKING SAME

CROSS-REFERENCE TO RELATED APPLICATIONS

The present applications claims priority from and is a continuation from U.S. patent application Ser. No. 11/157,147, filed Jun. 20, 2005, which is a divisional application of U.S. patent application Ser. No. 10/303,376, filed Nov. 25, 2002, now U.S. Pat. No. 6,923,829, all of which herein are incorporated by reference in their entireties.

BACKGROUND

The present invention relates generally to implantable expandable medical devices and more particularly to implantable endoluminal stents, covered-stents, stent-grafts and grafts employed to restore and maintain patency of anatomical passageways within a mammalian body. The dramatic success enjoyed by a variety of endoluminal implantable medical devices has largely been the result of their ability to be delivered utilizing minimally invasive techniques that significantly reduce the trauma to the patient. While there are many types of endoluminally-delivered implantable medical devices, the present invention relates specifically to generally tubular devices that are expandable from a first smaller diameter suitable for minimally invasive delivery to a second enlarge diameter suitable for restoring and maintaining patency of the anatomical passageway.

The most prevalent type of implantable expandable endoluminal device is the stent. Stents are typically used to treat occlusive and anuersymal disease or trauma and are, typically, generally tubular structural scaffolds typically consisting of latticed arrays of circumferential members and longitudinal members. The circumferential members typically permit the stent to radially expand from the first to the second diameter while the longitudinal members provide column strength and longitudinal flexibility. A variant of the stent, termed in the art either a stent-graft or covered stent, consists of a stent or other structural scaffold covered with a graft. Stent-grafts are devices typically employed for exclusionary purposes for purposes of creating a conduit, such as in excluding an abdominal aortic aneurysm, whereas covered stents are devices typically employed in treating occlusive conditions, such as coronary artery disease to restore patency to the coronary artery. Conventional stent-grafts and covered stents employ polymeric covers, such as polyester or expanded polytetrafluoroethylene that are either affixed to the stent by barbs or sutures or are retained on the stent by adhesion either to the stent or to an opposing graft surface.

Recently, radially expandable metallic grafts have been disclosed in co-pending, commonly assigned U.S. patent application Ser. Nos. 10/135,316 and Ser. No. 10/135,626, both filed Apr. 29, 2002, both of which are hereby expressly incorporated by reference, disclose a nitinol thin film graft having a pattern of microperforations that permit radial enlargement of the graft by geometric deformation of the microperforations.

Cardiovascular devices, in particular, should maintain vascular patency and prevent re-occlusion of the vascular system. There are two main types of implantable cardiovascular devices that are designed to restore and maintain vascular patency. The first type is a balloon expandable device that requires application of an externally applied force in order to radially distend the device. The second type is a self-expanding device that radially distends based upon inherent mechanical or material properties of the device, requires removal of a constraining force, and does not require application of an external force for radial distension. There are two main sub-types of self-expanding devices. A first sub-type consists of devices fabricated from traditional elasto-plastic materials, such as 316L stainless steel, that elastically recover from a constraining force applied to maintain the device in a smaller delivery diameter. The normalized strains typically associated with such traditional elasto-plastic materials is typically less than 1%. The second sub-type consists of devices fabricated from shape memory or superelastic materials that recover their shape under defined thermo-mechanical conditions. The recoverable strains associated with these materials can significantly excel 1%.

It is ironic that a major problem with existing self-expanding stents and their designs lies in their inherent spring properties. Current self-expanding stents are de facto elastically deformable along their longitudinal axis. In this manner, the device is capable of longitudinal bending and traversing the tortuous endoluminal pathways required to place the device at its intended in vivo site. Yet the very elastic nature of these devices imposes an inherent spring bias to the device which favors a zero-strain state in the normal or linear axial configuration. Thus, when longitudinally flexed, conventional self-expanding stents exhibit a positive strain and seek to return to the unbent or zero-strain normal conformation. When such a device is implanted into a non-linear vessel, in order to conform to the geometry of the vessel, the implanted device is in a strained longitudinal conformation that exerts continual, unevenly distributed stress against the vascular walls. This continual stress exerted on the vascular wall may ultimately lead to vascular injury and threaten clinical outcome.

Conventional stent designs have sought to control the inherent longitudinal spring bias by altering the geometric pattern of the structural components of the stent. Heretofore, however, there has been little focus in the art on altering the mechanical properties of selected regions of the material used to fabricate the implantable device. By selectively altering the mechanical properties of the device material, the device can have regions intended for plastic or pseudoplastic deformation and regions intended for elastic or pseudoelastic deformation. Thus, in accordance with the present invention there is provided within a single self-expanding device regions that are differentiated by their mechanical properties according to their intended functionality.

The term "elastic deformation," as used herein, is defined as a deformation of a traditional metal material caused by an applied load that is completely recoverable upon removal of the applied load. The elastic limit of a traditional metal is typically less than 1% strain.

The term "plastic deformation," as used herein, is defined as deformation of a traditional metal material caused by an applied load that cannot be completely recovered upon removal of the load because bonds have been broken.

The term "elasto-plastic," as used herein, is intended to mean materials that are capable of both elastic deformation and plastic deformation.

The term "pseudoelastic deformation," as used herein, is defined as a deformation caused by an applied load that is completely recoverable upon removal of the load and the limit of which is characterized by being significantly larger than the elastic limit of a traditional metal (8% strain in the case of nitinol). This phenomenon is caused by a load or stress induced solid-state phase change that is reversible upon removal of the load.

The term "pseudoplastic deformation," as used herein, is defined as a deformation caused by an applied load that requires some other action besides load removal, such as the application of heat, for complete recovery of the deformation. In pseudoplastic deformations, bonds have not been broken but, instead, have been reoriented or detwinned in the case of martensitic nitinol.

As used herein, the term "pseudometal" and "pseudometallic material" is defined as a biocompatible material which exhibits biological response and material characteristics substantially the same as biocompatible metals. Examples of pseudometallic materials include, for example, composite materials, ceramics, quartz, and borosilicate. Composite materials are composed of a matrix material reinforced with any of a variety of fibers made from ceramics, metals, or polymers. The reinforcing fibers are the primary load carriers of the material, with the matrix component transferring the load from fiber to fiber. Reinforcement of the matrix material may be achieved in a variety of ways. Fibers may be either continuous or discontinuous. Reinforcement may also be in the form of particles. Examples of composite materials include those made of carbon fibers, boron fibers, boron carbide fibers, carbon and graphite fibers, silicon carbide fibers, steel fibers, tungsten fibers, graphite/copper fibers, titanium and silicon carbide/titanium fibers.

A stress-strain curve for austenitic nitinol in which a sample is taken all the way to failure at a temperature above $A_F$ (finish of Austenitic transformation) can be separated into the following regions: elastic deformation of austenite, pseudoelastic deformation of austenite to stress induced martensite, elastic deformation of the stress induced martensite, plastic deformation of the stress induced martensite and fracture. Removal of the load at any point before the onset of plastic deformation of the stress induced martensite will result in complete recovery of the deformation.

Nitinol is in the thermally-induced martensite state if the material is brought to a temperature below $M_F$ (finish of martensitic transformation) and subsequently kept below $A_S$ (onset of austenitic transformation). If the material is sufficient deformed (greater than 0.5% strain) while in its thermally-induced martensite state and subsequently constrained at temperatures above $A_S$ it is still considered to be in its thermally-induced martensite state and not in a stress-induced martensite state. A stress-strain curve for martensitic nitinol in which a sample is taken all the way to failure at a temperature below $A_s$ can be separated into the following regions: elastic deformation of thermally induced martensite, pseudoplastic deformation of thermally induced martensite via detwinning, elastic deformation of the detwinned thermally induced martensite, plastic deformation of the detwinned thermally induced martensite and fracture. Removal of the load at any point before the onset of plastic deformation of the detwinned thermally induced martensite will result in complete recovery of the deformation when heated above $A_F$.

A standard procedure employed in the art to control the temperature-dependent mechanical properties of nickel-titanium alloys is to employ precipitation heat treatment. Heat treatment of a formed nickel-titanium device by subjecting the device to temperatures between 300-500° C. forces nickel-rich precipitates out of solution, i.e., out of the grains and into the intergranular boundaries. The result is a net increase in the titanium content of the grains and a concomitant increase in the transition temperature of the device. The use of precipitation heat treatment to selectively alter the mechanical properties of regions of a device based upon intended functionality has not, heretofore, been employed. Additionally, the use of vacuum deposition to control local bulk chemical content in precursor blanks and formed devices based upon intended functionality of the device has, heretofore, been unknown in the art of medical device fabrication.

SUMMARY OF THE INVENTION

Conventional implantable endoluminal devices rely principally on alterations in the geometry of the structural members of the device in order to affect its mechanical properties and intended functionality. In sharp contrast to this approach, the present invention alters the analytical paradigm by selectively changing the mechanical properties, such as the stress-strain characteristics, of functional regions within a device to change its behavior both during endoluminal delivery and when placed at the delivered in vivo site. By selectively controlling the mechanical properties of regions of the material used to fabricate the implantable device, a device having elastic, pseudoelastic, plastic, and/or pseudoplastic behavior in vivo may be produced.

The inventive implantable devices are characterized by having regions that are either plastically deformable or are sufficiently martensitic to behave pseudoplastically in vivo, and regions that are elastically deformable or sufficiently austenitic to behave pseudoelastically or superelastically in vivo. The inventive devices, therefore, have functional regions which are generally plastic and functional regions that are generally elastic. While those skilled in the art will appreciate that the present invention has broad application to many different types of implantable medical devices that require some type of geometric compliance, for ease of understanding, the present invention will be described with reference to cardiovascular devices, namely, stents, stent-grafts and grafts.

In the case of a stent, stent-graft, covered stent, or graft, for example, each of which must have the ability to be circumferentially expandable in vivo and longitudinally flexible for endoluminal delivery. Circumferentially expansive structural members may be formed of elastic, pseudoelastic or superelastic materials, have regions, such as hinge or articulation regions, that permit elastic, pseudoelastic or superelastic expansion of the circumferentially expansive structural members. Alternatively, the circumferentially expansive structural members may have regions having an $A_F$ value less than body temperature (i.e., 37° C.) or be sufficiently close to body temperature to behave elastically or pseudoelastically in vivo. Longitudinal flexibility is imparted by providing a series of longitudinal members that interconnect adjacent pairs of circumferentially expansive structural members.

It is desirable in accordance with the present invention, to fabricate the implantable medical devices from a metallic or pseudometallic material which has elasto-plastic, shape memory or pseudoelastic properties. In a preferred aspect of the invention, the implantable device is an endoluminal stent fabricated of shape memory alloy and includes a plurality of interconnected structural elements. Each of the structural elements is fabricated of shape memory material having austenitic regions and martensitic regions. The martensitic regions are sufficiently martensitic to operate with martensitic mechanical properties in vivo. The austenitic regions are sufficiently austenitic to operate with austenitic mechanical properties in vivo. While the martensitic regions are capable of undergoing phase transition to the austenite phase under appropriate conditions, the martensitic regions are formed such as to exhibit martensitic behavior under in vivo conditions. The martensitic regions are sufficiently martensitic such that the martensitic regions do not recover from a deformation event under in vivo conditions. The martensitic regions may be conditioned, either by selective annealing or by selective control over the local bulk chemical composition of the shape memory alloy to be sufficiently martensitic at their in vivo operating conditions to behave pseudoplastically in vivo. The austenitic regions are sufficiently austenitic at body temperature such that they will substantially recover any deformation.

With particular reference to implantable endoluminal stents, stents typically have structural members arranged in geometric patterns that permit both radial expansion and some measure of longitudinal flexibility. In order to radially expand, many current stent designs employ circumferential structures that radially enlarge by reorientation of linear members about a hinged section that interconnects adjacent linear members. A myriad of different geometries for the circumferential structures exist in the art, including, without limitation, zigzag, sinusoidal, undulating and slotted configurations. Longitudinal flexibility is typically provided by spacing apart adjacent circumferential structures and providing interconnecting members between adjacent pairs of circumferential structures. Again, a myriad of different geometries of the interconnecting members are known in the art, including, without limitation, linear, sinusoidal, curvilinear, zigzag or undulating configurations.

An aspect of the present invention provides a stent having a plurality of hinged strut members arrayed in end-to-end fashion forming a plurality of circumferential rings having a zigzag, sinusoidal or undulating configuration having peaks and valleys. A plurality of interconnecting members interconnect adjacent pairs of circumferential ring. The ring-like circumferential supports are composed of individual linear strut members interconnected at opposing ends of the strut members by generally U-shaped or V-shaped expansion hinge members. The individual interconnection members preferably have hinge members intermediate opposing ends of each interconnection member. The inventive stents are configured such that certain hinge regions are martensitic regions, while other hinge regions are austenitic regions. In this manner is generally accomplished by designing the stents so that certain hinge regions, or transition points where strut segments are connected to one another, have a superelastic characteristic while other hinge regions have a pseudoplastically deformable characteristic.

In accordance with a method of the present invention, the inventive implantable device is preferably formed by selectively heat-treating hinge regions of the devices to affect the mechanical properties of the material at the hinge regions. The inventive device may be fabricated by conventional wrought material or may be fabricated by nano-fabrication techniques. As more fully described in co-pending, commonly assigned U.S. Pat. No. 7,335,426, filed Aug. 2, 2002, the disclosure of which is hereby incorporated by reference, device-forming materials, such as metals and pseudometals may be vacuum deposited onto a substrate forming a thin film of material that may either be patterned during deposition, such as by depositing through a patterning mask or may be patterned post-deposition by photolithography or by etching. The martensitic regions may be formed by selective precipitation annealing of regions of the device or by locally controlling the chemical stoichiometry of the regions during the vacuum deposition process.

The plurality of expansion hinges, the plurality of longitudinal flexion hinges and the plurality of intermediate hinges may all have different material and/or mechanical properties from one another or from the strut members. For example, in accordance with one embodiment of the invention, the interconnection member hinges are made sufficiently martensitic so that they pseudoplastically deform permitting non-recoverable longitudinal flexion of the device, thereby minimizing unwanted vascular injury, and the expansion hinges are sufficiently austenitic, so that permit self-expansion of the device.

Thus, the implantable medical devices of the present invention have differential material and/or mechanical properties in different functional regions of the device. As an example, martensitic regions permit pseudoplastic deformation while the austenitic regions permit shape memory or superelastic deformation for in vivo self-expansion. The particular geometry and functionality of the implantable device, such as a stent, stent-graft or graft, will dictate which regions of the device are to operate martensiticly in vivo and which regions are to operate austeniticly in vivo.

As an example of attempts to provide implantable endoluminal devices with regions having different mechanical properties, U.S. Pat. Nos. 6,264,687 and 6,425,855, issued Jul. 24, 2001 and Jul. 30, 2002, respectively, describe a balloon expandable multi-laminate stent having superelastic articulated sections. The stent described in the '855 and '687 patents is a balloon expandable stent having plastically deformable circumferential stent sections and superelastic interconnecting sections between adjacent pairs of circumferential stent sections. While the stent construction is a multi-laminate, with a luminal layer of superelastic material and an abluminal layer of stainless steel, at the interconnections, the abluminal stainless steel layer is removed to expose only a single layer of superelastic material. The superelastic interconnecting sections are elastically compliant as the device traverses tortuosities in the vascular system to ease intraluminal delivery. The device is, however, non-self-expanding and the superelastic component is employed merely to increase longitudinal flexibility by adding an elastic component to an otherwise plastically deformable device. The superelastic interconnecting members will still exert deleterious elastic recoil against the vessel walls when implanted at a tortuous site.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

DETAILED DESCRIPTION OF THE INVENTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Generally speaking, the present invention pertains generally to self-expanding endoluminal devices and methods for their production, and more particularly to implantable self-expanding medical devices, such as endoluminal stents, having a generally tubular configuration formed of a plurality of structural support members in which geometric deformation of the plurality of structural support members causes a geometric expansion of the implantable medical device.

The endoluminal devices are made of biocompatible metals or pseudometals. Preferably, the endoluminal devices are fabricated so that they exhibit circumferential self-expansion, plastic or pseudoplastic flexibility in the longitudinal axis of the device and have negligible longitudinal elastic recoil, i.e., less than 20%, when the device is flexed along its longitudinal axis. Suitable biocompatible materials for use with the present invention include, for example, titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel. In accordance with the best mode presently contemplated for the present invention, the inventive implantable medical devices are fabricated of shape memory materials, such as nickel-titanium alloys or nitinol.

Figure 1:
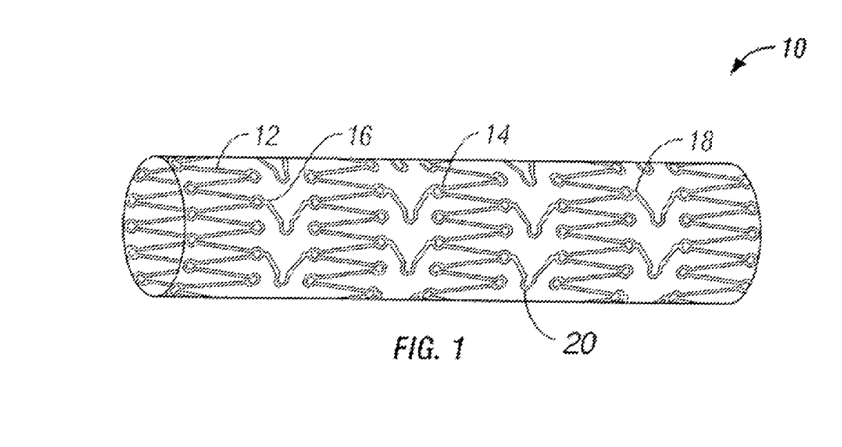
FIG. 1 is a perspective view of an implantable stent in accordance with the present invention in its unexpanded diameter.
Figure 2:
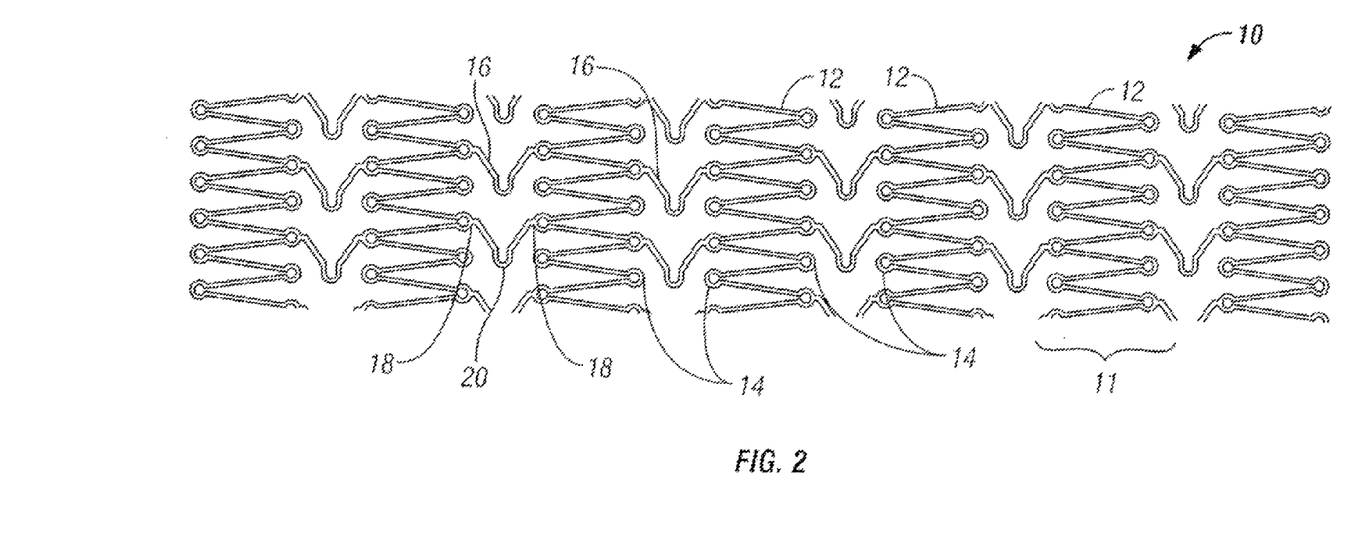
FIG. 2 is a plan view of a longitudinal section of the implantable stent in its unexpanded state.
Figure 3:
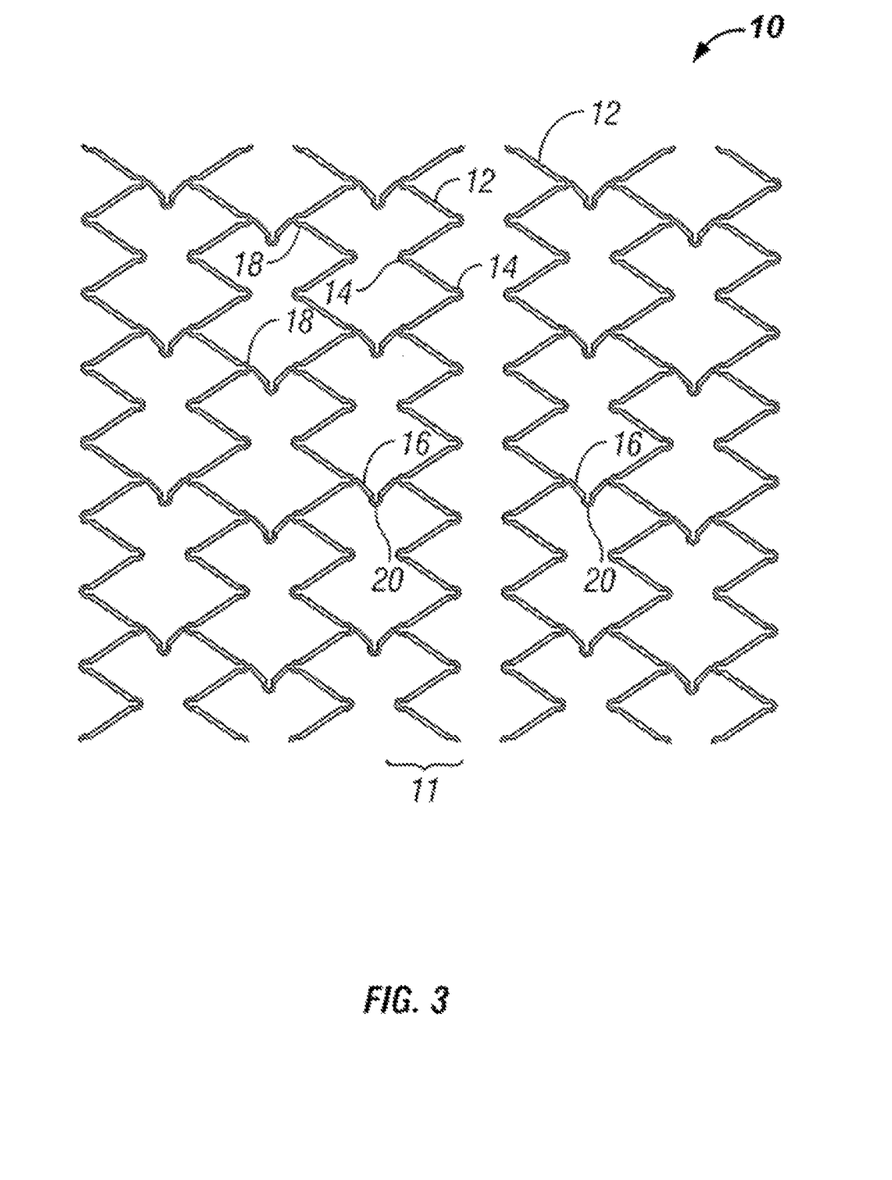
FIG. 3 is a plan view of a longitudinal section of the implantable stent in its expanded state.

Turning to FIGS. 1-3, there is illustrated an endoluminal stent 10 in accordance with the present invention. Endoluminal stent 10 has a plurality of strut members 12 each of which is interconnected with an adjacent strut member 12 by a first hinge member 14. The plurality of strut members 12 are interconnected by first hinge members 14 in end-to-end fashion forming a zig-zag, sinusoidal or undulating array, with the first hinge members forming successive peaks and valleys of the array. An entire array of strut members 12 interconnected by first hinge members 14 forms a circumferential ring member 11.

A plurality of circumferential ring members 11 are interconnected by interconnection members 16 that interconnect adjacent pairs of circumferential ring members 11. Connection points 18 interconnect the interconnection members 16 to the first hinge members 14 of the circumferential ring members 11. The interconnection members may have a generally linear geometry, may be curvilinear, may have a V- or U-shape, or be sinusoidal in shape. At least some of the interconnection members 16, and preferably all or substantially all of the interconnection members 16 further have at least one second hinge member 20 positioned along a length of the interconnection member 16.

In accordance with a preferred embodiment of the present invention, the endoluminal stent 10 is fabricated of nickel-titanium alloy and the first hinge members 14 are sufficiently austenitic at zero strain and body temperature conditions to behave pseudoelastically in vivo. In this manner, the first hinge members 14 act in a circumferentially self-expansive manner in vivo to diametrically expand the circumferential ring members 11 from a smaller delivery diameter depicted in FIGS. 1 and 2 to the enlarged diameter depicted in FIG. 3. The second hinge members 20 are preferably sufficiently martensitic to behave pseudoplastically under in vivo conditions and have an $A_S$ transition temperature above body temperature. By deforming pseudoplastically in vivo, the second hinge members 20 permit longitudinal flexibility of the device, effectively isolate stress transmission between adjacent pairs of circumferential ring members, and remain longitudinally deformable after a flexion load is released.

In accordance with a preferred embodiment of the present invention, the first hinge members 14 are sufficiently austenitic under in vivo conditions to allow at least about 90% recovery, preferably at least about 95% recovery, of an unstrained configuration of the device. Additionally, the second hinge members 20 are sufficiently martensitic under in vivo conditions to exhibit a substantially non-recoverable deformation of less than 1% upon application of a deforming load. Each of the interconnecting members 16 that have a second hinge member 20 therein will preferably have a martensite-austenite phase gradient, such that the second hinge member 20 is generally martensitic while the remaining non-hinge regions of the interconnecting member 16 are generally austenitic. It will be recognized that because the second hinge member 20 may be considered a region of the interconnection member 16, there are differential mechanical and material properties along the length of the interconnection member 16.

Alternatively, the second hinge members 20 may be configured to be sufficiently austenitic to behave pseudoelastically in vivo. Where the second hinge members 20 behave pseudoelastically, they are also capable of shape memory self-expansion, and may be used, for example, to compensate for any foreshortening by circumferential expansion of the stent 10.

While an endoluminal stent is depicted in the accompanying figures, it will be understood that this particular device, and the particular geometry of the device is for illustrative purposes only, and that other types of implantable self-expanding medical devices that require geometric deformation when implanted, such as stent-grafts, covered stents, grafts, embolic filters, valves, occluders, or the like are specifically contemplated by the present invention. Virtually any type of endoluminal self-expanding implantable medical device will benefit from the present invention. So long as the endoluminal self-expanding device relies upon circumferential expansion and has a component of longitudinal flexibility for delivery and implantation, differentiating function regions as plastic or pseudoplastic and elastic or pseudoelastic will aid in the deliverability, reducing luminal trauma and in vivo performance of the device. It will also be appreciated by those skilled in the art that depending upon the indication for the particular device, alternate geometries of the device are dictated by the particular indication, function and properties for the particular device.

Figure 4:
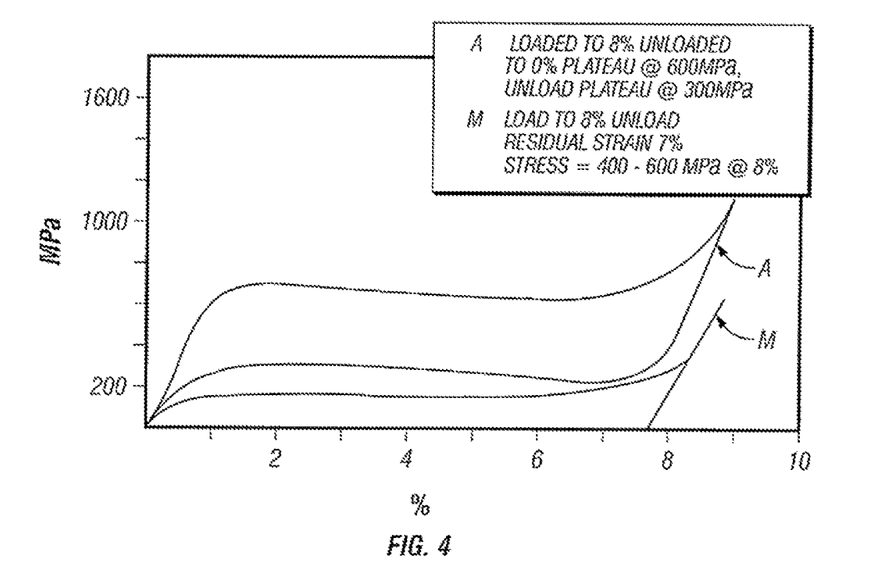
FIG. 4 is a stress-strain curve illustrating the stress-strain behavior of an inventive device including a curve M for the martensitic regions of the device and a curve A for the austenitic regions of the device.

FIG. 4 is a prototypical stress-strain curve at constant temperature and depicts the stress-strain behavior of martensite in Curve M and austenite Curve A regions of a device under the same stress-strain conditions. It will be readily understood that the behavior of the martensite regions and the behavior of the austenite regions under for a given applied stress, results in vastly different strain being developed in the material. For example, the austenite phase stress-strain curve, Curve A, is loaded to 8% strain with a loading plateau at 600 MPa, while it is fully recoverable by unloading to 0% strain with an unloading plateau at 300 MPa. In contrast, the martensite phase stress-strain curve exhibits loading to 8% with a loading plateau at about 200 MPa and a peak loading at about 400-600 MPa, while on unloading the material, there remains a residual strain in of about 7% in the material. Thus, under the same stress-strain and temperature conditions, the martensitic regions will behave pseudoplastically, while the austenite regions will behave superelastically.

Figure 5:
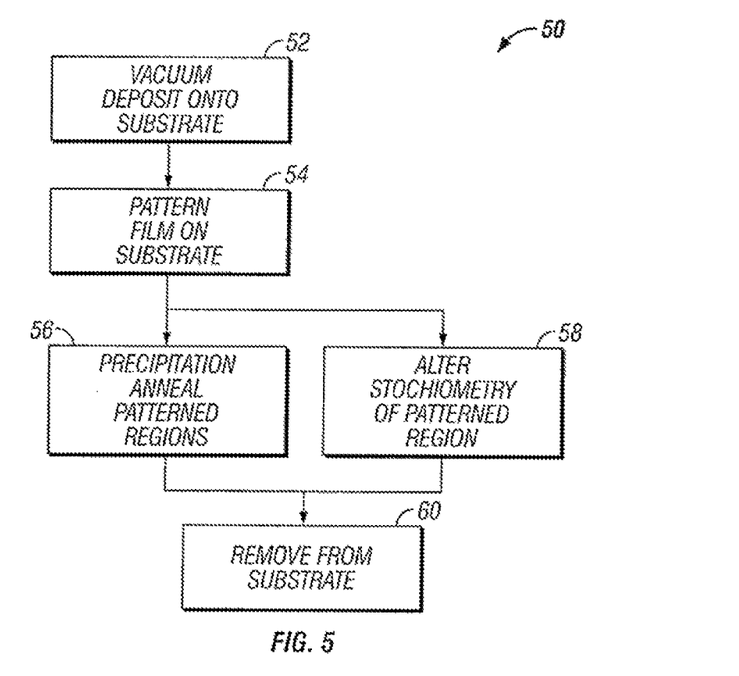
FIG. 5 is a process flow diagram depicting the method of fabricating the inventive implantable medical devices.

The method 50 of the present invention is depicted in FIG. 5. In accordance with the best mode for practicing the invention, The general method for vacuum depositing shape memory materials and fabricating implantable medical devices is set forth in co-pending, commonly assigned U.S. patent application Ser. No. 10/211,489, filed Aug. 2, 2002, and is hereby incorporated by reference. In accordance with the inventive method, a shape memory material, such as nitinol, is vacuum deposited onto a substrate in step 52. Vacuum deposition is preferably sputtering from either a nickel-titanium alloy target or a target having nickel and titanium elements onto a substrate. The substrate may be planar, cylindrical or have such other geometric shape as is desired for the implantable medical device. A pattern is imparted to the film on the substrate in step 54. The pattern may either be formed by selective deposition through a patterning mask, or by selective removal, such as by etching, of unwanted regions of the deposited film. Once the pattern is formed, martensitic regions may be formed in the pattern either by heat treatment at step 56 or by altering the chemical stoichiometry of a region at step 58. Local heat treatment may be accomplished in step 56 by applying focal heat to the desired region, such as by resistive heating applied through a point source, such as a soldering iron, or by laser focal heat treatment. Heat treatment causes nickel precipitation out of the grains. In order to achieve a maximum precipitation rate, heat treatment at 425° C. for between about 5 to 10 minutes has been found useful. Conversely, regions of the device may be heat treated at higher temperatures to drive nickel precipitates back into solution in the grain structure, thereby, altering the chemical stoichiometry and the transition temperature of the heat treated region. It has been found that heat treatment above 500° C. for between about 5 to 10 minutes will drive nickel precipitates back into solution in nickel-titanium alloys and reduce the transition temperature of the heat treated region.

Alternatively, the chemical stoichiometry of a region may be altered by either increasing the titanium content or lowering the nickel content of a selected region of the pattern to increase the transition temperature at the regions and have the martensite phase predominate at the operating temperature of the device. This may be accomplished by interposing a mask corresponding to the selected regions and vacuum depositing from a titanium-rich target through the mask and onto the substrate.

During deposition, the chamber pressure, the deposition pressure and the partial pressure of the process gases are controlled to optimize deposition of the desired species onto the substrate. As is known in the microelectronic fabrication, nano-fabrication and vacuum coating arts, both the reactive and non-reactive gases are controlled and the inert or non-reactive gaseous species introduced into the deposition chamber are typically argon and nitrogen. The substrate may be either stationary or moveable, either rotated about its longitudinal axis, or moved in an X-Y plane within the reactor to facilitate deposition or patterning of the deposited material onto the substrate. The deposited material may be deposited either as a uniform solid film onto the substrate, or patterned by (a) imparting either a positive or negative pattern onto the substrate, such as by etching or photolithography techniques applied to the substrate surface to create a positive or negative image of the desired pattern or (b) using a mask or set of masks which are either stationary or moveable relative to the substrate to define the pattern applied to the substrate. Patterning may be employed to achieve complex finished geometries of the resultant stent, both in the context of spatial orientation of the pattern as well as the material thickness at different regions of the deposited film, such as by varying the wall thickness of the material over its length to thicken sections at proximal and distal ends of the stent to prevent flaring of the stent ends upon radial expansion of the stent.

The stent may be removed from the substrate after stent formation by any of a variety of methods at step 60. For example, the substrate may be removed by chemical means, such as etching or dissolution, by ablation, by machining or by ultrasonic energy. Alternatively, a sacrificial layer of a material, such as carbon or aluminum, may be deposited intermediate the substrate and the stent and the sacrificial layer removed by melting, chemical means, ablation, machining or other suitable means to free the stent from the substrate.

The resulting stent may then be subjected to post-deposition processing to modify the crystalline structure, such as by annealing, or to modify the surface topography, such as by etching to affect and control heterogeneities on the blood flow surface of the stent. However, by fabricating the disclosed stents using vapor deposition techniques, the need for post-deposition processing of the patterned endoluminal stent, e.g., modifying the surface of the stent by mechanical, electrical, thermal or chemical machining or polishing is minimized or eliminated.

Physical vapor deposition fabrication of the inventive endoluminal implantable devices offers many advantages, including, for example, the ability to fabricate stents of complex geometries, ultra-fine dimensional tolerances on the order of Angstroms, the ability to control fatigue life, corrosion resistance, corrosion fatigue, inter- and intra-granular precipitates and their effect on corrosion resistance and corrosion fatigue, bulk material composition, bulk and surface material properties, radioopacity, and the ability to vary the transverse profiles, Z-axis thickness and X-Y-axis surface area of the stent structural elements in manners that affect the longitudinal flexibility, hoop strength, and radial expansion behavior and profile of the stent. Bulk material composition may be adjusted to employ elemental fractions in alloy compositions that are not feasible when using conventionally formed metals. This results in achieving the ability to tailor the alloy compositions in a manner that optimizes the alloy composition for a desired material or mechanical property. For example, nickel-titanium tubes exhibiting shape memory and/or superelastic properties were made employing in excess of 51.5 atomic percent nickel, which is not achievable using conventional working techniques due to high plateau stresses exhibited by the material. Specifically, the present inventors have fabricated nickel-titanium alloy tubes employing the method of the present invention that contain between 51.5 and 55 atomic percent nickel.

In a preferred embodiment of the present invention, the $A_S$ temperature of the martensitic regions of the inventive implantable medical device are preferably above body temperature so that a strain applied to the martensitic regions will invoke a pseudoplastic deformation. The austenite region preferably has an $A_F$ temperature below body temperature so that they remain austenitic in vivo to preserve their pseudoelastic properties in the body.

In loading the inventive implantable device for delivery using a delivery catheter, it is desirable that the device be brought to a temperature below $M_F$ and loaded into the catheter at a temperature below $A_S$. In this manner, the regions that will be austenitic in vivo exist in a thermally induced martensite phase before in vivo delivery.

The present invention provides, therefore, an implantable expandable medical device in which selected regions of the device are plastically deformable or sufficiently martensitic to behave pseudoplastically in vivo, and other regions are elastically deformable or are sufficiently austenitic to behave pseudoelastically in vivo. It is preferable that the regions of the device that are responsible for circumferential expansion be elastically or pseudoelastically deformable in order to effectuate circumferential self-expansion in vivo, while the regions of the device that are responsible for longitudinal flexibility be either plastically or pseudoplastically deformable in order to be compliant with the anatomical geometry both during and after delivery, without exerting an elastic recoil against the anatomical geometry.

While the present invention has been described with reference to its preferred embodiments, those skilled in the art will understand that the present invention has application across a broad range of expansible implantable medical devices that require expansion from a first smaller geometry to a second larger geometry and those that may benefit from having differential mechanical properties in different regions of the device material.

What is claimed is:

1. An implantable, geometrically expandable, generally tubular, nickel-titanium medical device, comprising:
   a. a plurality of circumferentially self-expansible members interconnected by a plurality of first hinge regions;
   b. a plurality of interconnecting members interconnecting adjacent pairs of circumferentially self-expansible members, the plurality of interconnecting members having a first portion and a second portion comprising a greater part of the interconnecting member than a second hinge member disposed between the first and second portions, the first and second portions being oblique to the second hinge member at a point immediately adjacent to a junction between the second hinge member and either the first or the second portions, wherein the majority of the second hinge member is martensitic in vivo and the first and second portions are austensitic in vivo;
   c. where each of the plurality of first hinge regions permits circumferential expansion of the device by at least one of elastic or pseudoelastic deformation in vivo; and
   d. where each of the plurality of second hinge regions is capable of deforming by at least one of plastic or pseudoplastic deformation along a longitudinal axis of the device in vivo under the influence of a flexing load.

2. The device according to claim 1, wherein each of the plurality of circumferentially self-expansible members further comprises a ring member having of a plurality of generally linear structural members interconnected at opposing ends thereof by one of the plurality of first hinge regions.

3. The device according to claim 2, wherein each of the plurality of generally linear structural members and each of the plurality of first hinge regions further comprise a nickel-titanium alloy in a sufficiently austenite phase to behave pseudoelastically in vivo.

4. The device according to claim 3, wherein each of the plurality of interconnecting members have regions thereof that are in a sufficiently austenitic phase to operate in at least one of an elastic or pseudoelastic manner in vivo.

5. The device according to claim 1, wherein each of the plurality of circumferentially self-expansible members further comprises a material selected from the group consisting of biocompatible metals, metal alloys and pseudometals that are capable of behaving elastically or pseudoelastically in vivo.

6. The device according to claim 5, wherein each of the plurality of interconnecting members further comprises a material selected from the group consisting of biocompatible metals, metal alloys and pseudometals that are capable of behaving plastically or pseudoplastically in vivo.

7. An implantable, expandable medical device comprising:
   a. a plurality of circumferential ring members, each having a plurality of generally linear members interconnected by a plurality of first hinge members; and
   b. a plurality of interconnecting members each having at least one second hinge member disposed between non-hinge regions, wherein the interconnecting members interconnect adjacent pairs of the circumferential ring members;
   wherein the non-hinge regions are oblique to the second hinge member at a point immediately adjacent to a junction between the second hinge member and either of the non-hinge regions, wherein a majority of at least some of the second hinge members is martensitic, while the non-hinge regions of the interconnecting members are generally austenitic, wherein the second hinge members are substantially non-collinear with the non-hinge regions of the interconnecting members when the device is in an expanded state, and wherein the non-hinge regions comprise a greater part of the interconnecting members than the second hinge members.

8. The device according to claim 7, wherein each of the plurality of interconnecting members further comprises a material having a martensite-austenite phase gradient therein.

9. The device according to claim 7, wherein each of the plurality of circumferential ring members further comprises a material selected from the group consisting of elastically or pseudoelastically deformable biocompatible metals, metal alloys and pseudometals.

10. The device according to claim 7, wherein each of the plurality of interconnecting members further are in a sufficiently austenite phase to behave pseudoelastically in vivo.

11. The device according to claim 7, wherein each of the plurality of interconnecting members further comprise a shape memory alloy in a sufficiently martensite phase to behave pseudoplastically in vivo.

12. The device according to claim 7, wherein each of the plurality of interconnecting members further comprises a material selected from the group consisting of plastically or pseudoplastically deformable biocompatible metals, metal alloys and pseudometals.

13. An implantable medical device, comprising:
a generally tubular member comprising a plurality of circumferential ring members each having a plurality of strut members interconnected by first hinge members; and
a plurality of interconnecting members configured to connect adjacent pairs of circumferential ring members, each of the interconnecting members having a first portion, a second portion, and a second hinge member disposed between the first and second portions, the first and second portions being oblique to the second hinge member at a point immediately adjacent to a junction between the second hinge member and either the first or the second portions;
where the plurality of strut members, the first hinge members, and the first and second portions of the plurality of interconnecting members have an austenitic phase in vivo to permit at least one of elastic or pseudoelastic circumferential expansion in vivo;
where a majority of at least some of the second hinge members is martensitic to permit plastic or pseudoplastic deformation of the tube member along the longitudinal axis of the device in vivo and the first portion and the second portion are austenitic and comprise a greater part of the interconnecting members than the second hinge members; and
where the second hinge members are substantially non-collinear with other regions of the interconnecting members when the second hinge members behave plastically or pseudoplastically under in vivo conditions.

14. The implantable medical device according to claim 13, wherein the generally tubular member further comprises a nickel-titanium alloy.

15. The implantable medical device according to claim 13, wherein the first hinge regions further comprise regions that are sufficiently austenitic under in vivo conditions to allow at least about 90% recovery of an unstrained configuration of the device.

16. The implantable medical device according to claim 13, wherein the second hinge regions further have a higher transition temperature than the remainder of the generally tubular member.

17. The implantable medical device according to claim 13, wherein at least some of the strut members, at least some of the first hinge members, and at least some of the interconnecting members comprise a material selected from the group consisting of biocompatible metals, metal alloys and pseudometals that are capable of behaving elastically or pseudoelastically in vivo.

18. The implantable medical device according to claim 13, wherein at least some of the plurality of strut members, at least some of the first hinge members, and at least some of the interconnecting members comprise a material selected from the group consisting of biocompatible metals, metal alloys and pseudometals that are capable of behaving plastically or pseudoplastically in vivo.

* * * * *